(12) United States Patent
Choudhary et al.

(10) Patent No.: US 10,625,180 B2
(45) Date of Patent: Apr. 21, 2020

(54) MANUFACTURING METHOD

(71) Applicant: Arexis AB, Stockholm (SE)

(72) Inventors: Sureshkumar Choudhary, Gaithersburg, MD (US); Tesfu Mezghebe, Gaithersburg, MD (US); Mary Houchin, Gaithersburg, MD (US); Eric Vernooij, Nijmegen (NL); Marjo Peters, Nijmegen (NL); Marta Corcoran, Gaithersburg, MD (US); Yoen Joo Kim, Gaithersburg, MD (US); Mingyan Cao, Gaithersburg, MD (US)

(73) Assignee: Arexis AB, Stockholm (SE)

( * ) Notice: Subject to any disclaimer, the term of this patent is extended or adjusted under 35 U.S.C. 154(b) by 362 days.

(21) Appl. No.: 15/522,472

(22) PCT Filed: Oct. 30, 2015

(86) PCT No.: PCT/US2015/058241
§ 371 (c)(1),
(2) Date: Apr. 27, 2017

(87) PCT Pub. No.: WO2016/069999
PCT Pub. Date: May 6, 2016

(65) Prior Publication Data
US 2017/0333812 A1 Nov. 23, 2017

Related U.S. Application Data

(60) Provisional application No. 62/073,459, filed on Oct. 31, 2014.

(51) Int. Cl.
*B01D 19/00* (2006.01)
*C07K 16/00* (2006.01)
*C07K 16/10* (2006.01)

(52) U.S. Cl.
CPC .......... *B01D 19/0036* (2013.01); *C07K 16/00* (2013.01); *C07K 16/1027* (2013.01); *C07K 2317/24* (2013.01); *C07K 2317/565* (2013.01)

(58) Field of Classification Search
CPC .......................... B01D 19/00; B01D 19/0036
See application file for complete search history.

(56) References Cited

U.S. PATENT DOCUMENTS

| | | | |
|---|---|---|---|
| 5,314,995 A | 5/1994 | Fell, Jr. et al. | |
| 5,545,807 A | 8/1996 | Surani et al. | |
| 5,591,669 A | 1/1997 | Krimpenfort et al. | |
| 5,824,307 A | 10/1998 | Johnson | |
| 5,939,598 A | 8/1999 | Kucherlapati et al. | |
| 6,500,239 B2 | 12/2002 | Castellano et al. | |
| 6,818,216 B2 | 11/2004 | Young et al. | |
| 6,955,717 B2 | 10/2005 | Johnson et al. | |
| 7,229,618 B2 | 6/2007 | Johnson et al. | |
| 2005/0109078 A1 | 5/2005 | Chen et al. | |
| 2006/0034827 A1 | 2/2006 | Oliver et al. | |
| 2006/0216284 A1 | 9/2006 | Tous et al. | |
| 2007/0169434 A1 | 7/2007 | Kinney et al. | |
| 2007/0175538 A1 | 8/2007 | Rothbauer et al. | |

FOREIGN PATENT DOCUMENTS

| | | |
|---|---|---|
| EP | 0 396 387 B1 | 12/1993 |
| WO | WO 89/12624 A2 | 12/1989 |
| WO | WO 91/14438 A1 | 10/1991 |
| WO | WO 92/08495 A1 | 5/1992 |
| WO | WO 2014/071344 A2 | 5/2014 |

OTHER PUBLICATIONS

Brüggemann et al., "Designer mice: the production of human antibody repertoires in transgenic animals," *Year in Immunology*, 1993; 7:33-40.
Clackson et al., "Making antibody fragments using phage display libraries," *Nature*, 1991; 352(6336):624-628.
Jakobovits et al., "Analysis of homozygous mutant chimeric mice: Deletion of the immunoglobulin heavy-chain joining region blocks B-cell development and antibody production," *PNAS USA*, 1993; 90:2551-2555.
Jakobovits et al., "Germ-line transmission and expression of a human-derived yeast artificial chromosome," *Nature*, 1993; 362(6417):255-258.
Johnson et al., "Development of a humanized monoclonal antibody (MEDI-493) with potent in vitro and in vivo activity against respiratory syncytial virus," *Journal of Infectious Diseases*, 1997; 176:1215-1224.
Marks et al. "By-passing immunization. Human antibodies from V-gene libraries displayed on phage," *Journal of Molecular Biology*, 1991; 222(3):581-597.
Marks et al., "By-passing immunization: building high affinity human antibodies by chain shuffling," *Biotechnology (NY)*, 1992; 10(7):779-783.
McCafferty et al., "Phage antibodies: filamentous phage displaying antibody variable domains," *Nature*, 1990; 348(6301):552-554.
Waterhouse et al., "Combinatorial infection and in vivo recombination: a strategy for making large phage antibody repertoires," *Nucleic Acids Research*, 1993; 21(9):2265-2266.

(Continued)

*Primary Examiner* — Stacy B Chen
(74) *Attorney, Agent, or Firm* — Mueting, Raasch & Gebhardt, P.A.

(57) ABSTRACT

This application is directed to a method of producing vials containing a composition comprising a recombinant protein. In some embodiments, the method comprises: (a) providing a container containing a composition comprising a recombinant protein optionally where the container has been stored under positive pressure; (b) applying a vacuum to the container containing a composition comprising a recombinant protein; (c) allowing the vacuum to degas the composition; and (d) filling vials with the de gassed composition comprising a recombinant protein.

19 Claims, 7 Drawing Sheets
Specification includes a Sequence Listing.

(56) References Cited

OTHER PUBLICATIONS

WHO Expert Committee on Biological Standardization, "Requirements for the Use of Animal Cells as in vitro Substrates for the production of biologicals: Requirements for Biological Substances No. 50," WHO Technical Report Series, No. 878, 1998; 108 pages (Annex 1—pp. 19-56).
International Preliminary Report on Patentability, PCT Application No. PCT/US2015/058241, dated May 2, 2017, 6 pages.
International Search Report, PCT Application No. PCT/US2015/058241, dated Jun. 30, 2016, 3 pages.
Written Opinion of the International Searching Authority, PCT Application No. PCT/US2015/058241, dated Jun. 30, 2016, 5 pages.

A

B

A

B

MANUFACTURING METHOD

CONTINUING APPLICATION DATA

This application is the § 371 U.S. National Stage of International Application No. PCT/US2015/058241, filed Oct. 30, 2015, which claims the benefit of U.S. Provisional Application Ser. No. 62/073,459, filed Oct. 31, 2014, the disclosures of which are incorporated by reference herein in their entireties.

DESCRIPTION

This application contains a Sequence Listing electronically submitted via EFS-Web to the United States Patent and Trademark Office as an ASCII text filed entitled "RSVAB-305WO1_ST25" having a size of 12 kilobytes and created on Oct. 30, 2015. The electronically submitted Sequence Listing serves as both the paper copy required by 37 CFR 51.821(c) and the CRF required by 51.821(e). The information contained in the Sequence Listing is incorporated by reference herein.

FIELD

A method of producing vials containing a composition comprising a recombinant protein.

BACKGROUND

Recombinant proteins, such as antibodies, have been used in the treatment of various diseases and conditions and are generally derived from cell culture, using either eukaryotic or prokaryotic cell lines. Recombinant proteins, such as antibodies, used in pharmaceutical applications must have a high level of purity, especially in regard to contaminants from the cell culture, including cellular protein contaminants, cellular DNA contaminants, viruses and other transmissible agents. See "WHO Requirements for the use of animal cells as in vitro substrates for the production of biologicals: Requirements for Biological Substances No. 50." No. 878. Annex 1, 1998. Many recombinant proteins, such as antibodies, are packaged into single use containers or small multi-use containers in the form of vials. When produced in vials, such as clear glass vials, the appearance of both the composition comprising the recombinant protein and the vial itself are optimally preserved. Any visual defects in the vial or the compositions can cause unnecessary anxiety for patients and/or physicians. While there may be no degradation of the product and while it may be medically acceptable, either the company producing the vials, pharmacies, treating physicians, or patients may choose to reject the vials on the basis of their appearance only.

Thus there is a need an improved pharmaceutical manufacturing process to ensure that rings are not formed on the vials used to package compositions comprising a recombinant protein.

SUMMARY

In accordance with the description, a method of producing vials containing a composition comprising a recombinant protein comprises:
a. providing a container containing a composition comprising a recombinant protein optionally wherein the container has been stored under positive pressure;
b. applying a vacuum to the container;
c. allowing the vacuum to degas the composition; and
d. filling vials with the degassed composition comprising a recombinant protein.

In one aspect, the recombinant protein is Synagis®.

In one aspect, a method of isolating Synagis® from a composition comprising Synagis® comprises:
a. performing an ion exchange chromatography process on the composition;
b. performing an affinity purification process on the composition; and
c. performing a filtration process on the composition;
d. degassing the composition before filling vials with the composition, wherein a final product comprising Synagis® results from (a), (b), and (c), wherein the final product is suitable for administration to a human and has a DNA concentration of ≤0.5 pg/mg, and wherein the method does not comprise adding benzonase to the composition.

In another aspect, a method of isolating Synagis® from a composition comprising Synagis® comprises:
a. performing a cation exchange chromatography process on the composition to form a first product comprising Synagis®;
b. adding a buffer to the first product to form a buffered product;
c. performing an affinity purification process on the buffered product to form a second product comprising Synagis®;
d. performing a filtration process on the second product to form a third product comprising Synagis®;
e. performing a viral inactivation process on the third product; and formulating the third product to form a final product comprising Synagis®, wherein the final product is suitable for administration to a human and has a DNA concentration of ≤0.5 pg/mg; and
f. degassing the composition before filling vials with the composition, wherein the method does not comprise adding benzonase to the composition.

In another embodiment, a method of isolating Synagis® from a composition comprising Synagis® comprises at least three of (a)-(e) and wherein the method further comprises (f):
a. performing a cation exchange chromatography process on the composition;
b. performing an affinity purification process on the composition;
c. performing an ultrafiltration process on the composition;
d. performing a viral inactivation process on the composition; and
e. performing an anion exchange chromatography process on the composition;
f. degassing the composition before filling vials with the composition,
g. wherein the product resulting from the at least three of (i)-(v) comprises Synagis® and is suitable for administration to a human and has a DNA concentration of ≤0.5 pg/mg; and wherein the method does not comprise adding benzonase to the composition.

In one embodiment, the step of degassing the composition before filling vials with the composition comprises
a. providing a container containing a composition comprising a recombinant protein optionally wherein the container has been stored under positive pressure;
b. applying a vacuum to the container containing a composition comprising a recombinant protein;

c. allowing the vacuum to degas the composition; and
d. filling vials with the degassed composition comprising a recombinant protein.

In one aspect, the composition comprises:

a. a heavy chain having the amino acid sequence SEQ ID NO: 1 and a light chain having the amino acid sequence of SEQ ID NO: 6;
b. a heavy chain variable region of SEQ ID NO:1 or SEQ ID NO: 2 and a light chain variable region of the light chain SEQ ID NO:6; or
c. a H1 complementarity determining region (CDR) having the amino acid sequence TSGMSVG (SEQ ID NO: 3), a H2 CDR having the amino acid sequence DIWWDDKKDYNPSLKS (SEQ ID NO: 4), a H3 CDR having the amino acid sequence SMITNWYFDV (SEQ ID NO: 5); a L1 CDR having the amino acid sequence KCQLSVGYMH (SEQ ID NO: 7), a L2 CDR having the amino acid sequence DTSKLAS (SEQ ID NO: 8), and a L3 CDR having the amino acid sequence FQGSGYPFT (SEQ ID NO:9).

In one embodiment, the container containing a composition comprising a recombinant protein has been stored under positive pressure.

In another embodiment, a vacuum is applied for from about 12 hours to about 5 days. In another embodiment, a vacuum is applied for from about 1 day to about 4 days. In one embodiment, a vacuum is applied from about 50 to about 268 mbar. In another embodiment, a vacuum is applied that is greater than about 50 and less than or equal to about 268 mbar. In another embodiment, a vacuum is applied that is from about 60 to about 268 mbar. In one mode, a vacuum is applied at about 99 or about 268 mbar.

In one aspect, a vacuum is applied to a volume of a composition comprising a recombinant protein of from about 20 L to about 250 L. In another aspect, a vacuum is applied to a volume of a composition of about 40 L, about 50 L, about 65 L, or about 125 L. In one embodiment, the container may be larger than the volume of the composition. In one embodiment, no more than about 50 L of composition is present in an about 65 L tank. In one embodiment, no more than about 76 L of composition is present in an about 125 L tank. In one embodiment, about 46.5 L of composition is present in an about 65 L tank. In another embodiment, about 68.1 L of composition is present in an about 125 L tank.

In one mode, a bubble indicator is at least about 5.9 and is calculated using the following formula:

$$BI=(h_a*t*1000)/(h_1*PV), \text{ wherein}$$

V=volume of solution (mL)
P=degassing vacuum (mbar)
t=degassing time (hr)
$h_1$=height of liquid (cm) (calculated assuming tank is cylinder) and
$h_a$=height of air/headspace (cm).

In another mode, the composition comprising the recombinant protein does not comprise a surfactant. In another mode, a surfactant is not added to the composition comprising the recombinant protein. In another mode, the composition, when filled in at least one vial, does not form a ring on the air-liquid-glass interface of the vial. In a yet further mode, the composition, when filled in at least one vial, does not form a ring on the surface of the vial. In one embodiment, the composition does not comprise bubbles after degassing. In a further embodiment, the composition, after degassing and when being filled into at least one vial, does not comprise bubbles in vial fill lines or other tubing used in manufacturing.

In a further mode, the protein concentration of the recombinant protein in the composition comprising a recombinant protein is from about 0.1 mg/mL to about 1000 mg/mL. In a further aspect, the protein concentration is about 100 mg/mL.

In one mode, omitting the degassing step results in an accumulation of bubbles in the composition. In another mode, omitting the degassing step results in an accumulation of bubbles in the composition in fill lines. In a further aspect, omitting the degassing step results in a deposition of particles at air-liquid-glass interface of a vial containing the composition. In a further embodiment, the deposition of particles when omitting the degassing step is a deposition comprising the recombinant protein. In a further mode, the deposition of particles forms a ring on the vial.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 1A and B show the fill line, with FIG. 1A showing a picture of the fill line at the start of the fill process for the composition degassed at 268 mbar and FIG. 1B showing a picture of the end of the fill process (8.4 kg fill) for the composition degassed at 268 mbar.

DESCRIPTION OF THE SEQUENCES

Figure 1:
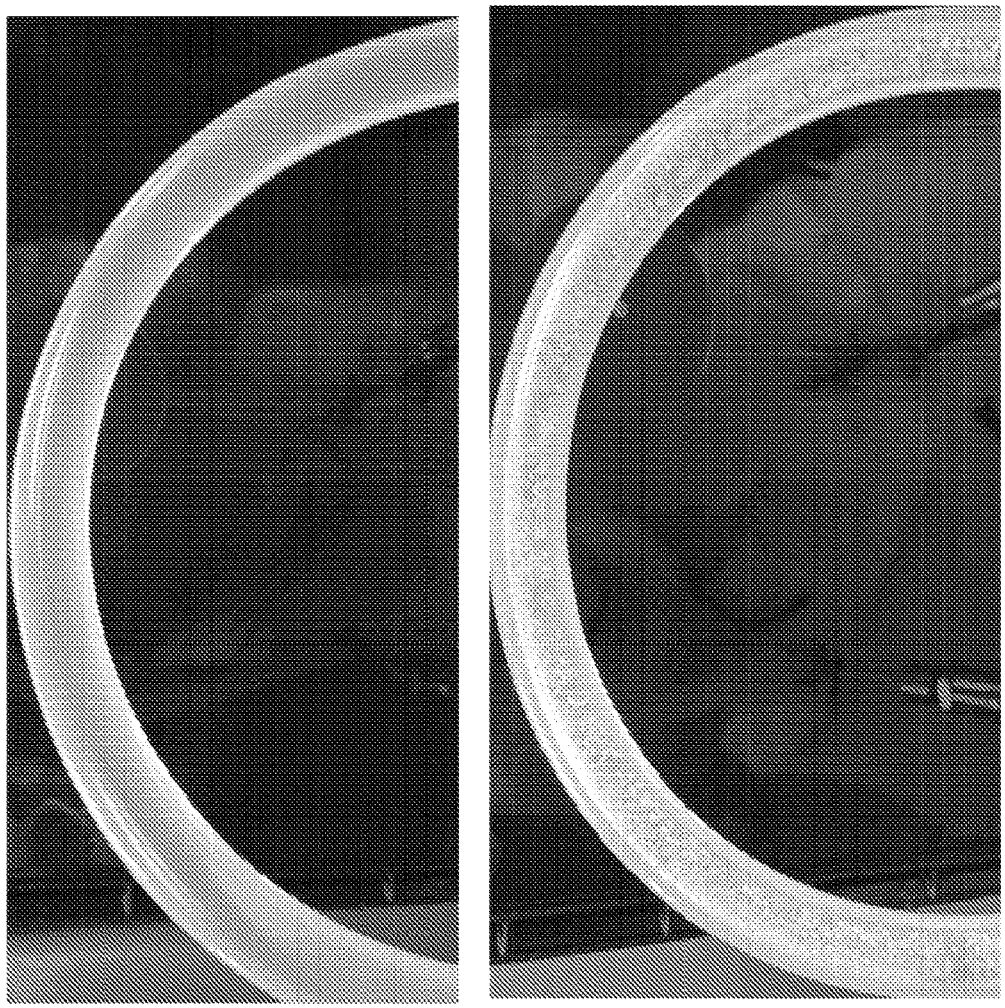
FIGS. 1A-B show, in a study of the impact of vacuum on a 2-day degassing process.

TABLE 1 provides a listing of certain sequences referenced herein.
Table 1: Description of the Sequences

| Description | Sequences | SEQ ID NO |
|---|---|---|
| Synagis ® heavy chain variable region | QVTLRESGPALVKPTQTLTLICTFSGFSLSTSGMSVGW IRQPPGKALEWLADIWWDDKKDYNPSLKSRLTISKDTS KNQVVLKVTNMDPADTATYYCARSMITNWYFDVWGAGT TVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKRVEPKSCDKTHT CPPCPAPELLGGPSVFLFPPKPKDTLMISRTPEVTCVV VDVSHEDPEVKFNWYVDGVEVHNAKTKPREEQYNSTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGK | 1 |
| Synagis ® heavy chain $F_{AB}$ | QVTLRESGPALVKPTQTLTLICTFSGFSLSTSGMSVGW IRQPPGKALEWLADIWWDDKKDYNPSLKSRLTISKDTS KNQVVLKVTNMDPADTATYYCARSMITNWYFDVWGAGT TCTCSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKRVEPKSCDKTH | 2 |
| Synagis ® heavy chain CDR1 | TSGMSVG | 3 |
| Synagis ® heavy chain CDR2 | DIWWDDKKDYNPSLKS | 4 |
| Synagis ® heavy chain CDR3 | SMITNWYFDV | 5 |
| Synagis ® light chain variable region | DIQMTQSPSTLSASVGDRVTITCKCQLSVGYMHWYQQK PGKAPKLLIYDTSKLASGVPSRFSGSGSGTEFTLTISS LQPDDFATYYCFQGSGYPPTFGGGTKLEIKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC | 6 |
| Synagis ® light chain CDR1 | KCQLSVGYMH | 7 |
| Synagis ® light chain CDR2 | DTSKLAS | 8 |
| Synagis ® light chain CDR3 | FQGSGYPFT | 9 |

DESCRIPTION OF THE EMBODIMENTS

I. Preparation of a Degassed Composition which does not Form a Vial Ring

It has been found that a ring may form on the vial of certain compositions comprising a recombinant protein. By "ring", this application refers to particle deposits at air-liquid-glass interface of a vial or other container leading to a visually-apparent round or oval cosmetic defect on the vial or other container. In one embodiment, the composition comprising a recombinant protein does not comprise a surfactant. In one embodiment, the composition comprising a recombinant protein does not have surfactant added during its manufacturing process. In certain instances, the composition comprising a recombinant protein has been stored under positive pressure for at least about 24 hours, at least about 36 hours, or at least about 48 hours, at least about 3 days, at least about 4 days, at least about 1 week, at least about 1 month, at least about 6 months, at least about 1 year, at least about 2 years, at least about 3 years.

Surprisingly it has been determined that degassing these compositions though application of a vacuum prevent ring formation on the vial containing these compositions comprising a recombinant protein.

In one embodiment, the degassing step is conducted after the composition is stored under positive pressure for at least about 24 hours, at least about 36 hours, or at least about 48 hours, at least about 3 days, at least about 4 days, at least about 1 week, at least about 1 month, at least about 6 months, at least about 1 year, at least about 2 years, at least about 3 years. In another embodiment, the composition comprising a recombinant protein may be stored under positive pressure after the degassing step for no more than about 16 hours, no more than about 12 hours, no more than about 8 hours, no more than about 6 hours, no more than about 4 hours, no more than about 3 hours, no more than less than about 2 hours, no more than about 90 minutes, no more than about 60 minutes, or no more than about 30 minutes. In another embodiment, the composition comprising a recombinant protein may be stored under positive pressure after the degassing step for no more than about 1 day, no more than about 2 days, no more than about 3 days, or for less than about 4 days.

A. Application of Vacuum

A variety of factors affect the ability of a vacuum to degas a composition comprising a recombinant protein, including, but not limited to, the strength of the vacuum, the duration of time the vacuum is applied, as well as properties of the container and solution (such as, but not limited to) the volume of the solution, the height of the liquid, and the height of the air/headspace. The amount of vacuum and the duration of vacuum that may be applied in any given circumstance may vary and may be determined qualitatively, by running a test batch and observing whether the degassing is sufficient to accomplish any goals. Alternatively, and in only certain embodiments, the amount of vacuum and the duration of the vacuum may be determined using a bubble indicator calculation according to the following formula:

$BI=(h_a*t*1000)/(h_1*PV)$, wherein

V=volume of solution (mL)
P=degassing vacuum (mbar)
t=degassing time (hr)
$h_1$=height of liquid (cm) (calculated assuming tank is cylinder) and
$h_a$=height of air/headspace (cm).

In one embodiment, the bubble indicator is at least about 12, at least about 11, at least about 10, at least about 9, at least about 8, at least about 7, at least about 6, or at least about 5.9.

In one embodiment, a vacuum is applied from about 50 to about 268 mbar. In another embodiment, a vacuum is applied that is greater than about 50 and less than or equal to about 268 mbar. In another embodiment, a vacuum is applied that is from about 60 to about 268 mbar. In one mode, a vacuum is applied at about 99 or about 268 mbar.

In one aspect, a vacuum is applied to a volume of a composition comprising a recombinant protein of from about 20 L to about 250 L or from about 40 L to about 70 L. In another aspect, a vacuum is applied to a volume of a composition of about 40 L, about 50 L, about 65 L, or about 125 L. In one embodiment, the container may be larger than the volume of the composition. In one embodiment, no more than about 50 L of composition is present in an about 65 L tank. In one embodiment, no more than about 76 L of composition is present in an about 125 L tank. In one embodiment, about 46.5 L of composition is present in an about 65 L tank. In another embodiment, about 68.1 L of composition is present in an about 125 L tank.

In one embodiment, the vacuum is applied for from about 46 hours to about 5 days. In one embodiment, the vacuum is applied for from about 2 days to about 4 days.

II. Selected Benefits of Degassing Step

A variety of benefits of the degassing step may be described as follows; however, not all benefits may be present in every situation. In one aspect, the degassing step allows the composition comprising a recombinant protein to be stored under positive pressure. In another embodiment, the composition comprising the recombinant protein does not comprise a surfactant. In another embodiment, a surfactant is not added to the composition comprising the recombinant protein.

In another aspect, the degassing step prevents the accumulation of bubbles in the composition comprising a recombinant protein. This may be assessed by omitting the degassing step, resulting in an accumulation of bubbles in the composition comprising a recombinant protein. In another aspect, the degassing step prevents an accumulation of bubbles in fill lines used to fill vials with the composition comprising a recombinant protein. This may be assessed by omitting the degassing step, resulting in an accumulation of bubbles in the fill lines used to fill vials with the composition comprising a recombinant protein.

In one embodiment, the degassing step prevents the deposition of particles at the air-liquid-gas interface of a vial containing a composition comprising a recombinant protein. This may be assessed by omitting the degassing step, resulting in a deposition of particles at air-liquid-glass interface of a vial containing a composition comprising a recombinant protein. In one aspect, the deposition of particles comprises the recombinant protein. In another embodiment, the deposition of particles forms a ring on the vial.

III. Compositions Comprising a Recombinant Protein

This process can be applied to a plurality of compositions comprising a recombinant protein. In one embodiment, the recombinant protein is an antibody. In another embodiment, the recombinant protein is an antibody against RSV.

In some embodiments, the antibody is Synagis® (Palivizumab) (MedImmune). Synagis® is a recombinant humanized (chimeric murine-human) IgG1kappa monoclonal antibody glycoprotein with specificity for an epitope in the A antigenic site of the F (fusion) protein of respiratory syncytial virus (RSV). Synagis® can be expressed from a stable murine (mouse) myeloma cell line (NSO). In some commercial embodiments, Synagis® is composed of two heavy chains (50.6 kDa each) and two light chains (27.6 kDa each), contains 1-2% carbohydrate by weight and has a molecular weight of 147.7 kDa±1 kDa (MALDI-TOF).

In some embodiments, a Synagis® antibody has a heavy chain having the amino acid sequence SEQ ID NO: 1 and a light chain having the amino acid sequence of SEQ ID NO: 6. In some embodiments, a Synagis® antibody includes the heavy chain variable region of the heavy chain amino acid sequence SEQ ID NO:1 or the heavy chain FAB amino acid sequence SEQ ID NO: 2 and the light chain variable region of the light chain amino acid sequence SEQ ID NO:6. In some embodiments, a Synagis® antibody includes a heavy chain H1 complementarity determining region (CDR) having the amino acid sequence TSGMSVG (SEQ ID NO: 3), a heavy chain H2 CDR having the amino acid sequence DIWWDDKKDYNPSLKS (SEQ ID NO: 4), a heavy chain H3 CDR having the amino acid sequence SMITNWYFDV (SEQ ID NO: 5); a light chain L1 CDR having the amino acid sequence KCQLSVGYMH (SEQ ID NO: 7), a light chain L2 CDR having the amino acid sequence DTSKLAS (SEQ ID NO: 8), and a light chain L3 CDR having the amino acid sequence FQGSGYPFT (SEQ ID NO:9). The Synagis® antibody and its amino acid sequence are disclosed, for example, in Johnson et al., 1997, *J. Infec. Dis* 76:1215-1224, and U.S. Pat. No. 5,824,307, which are both incorporated by reference for the description of the Synagis® antibody and its amino acid sequence.

In one embodiment, the recombinant protein is motavizumab (MEDI-524). The VH and VL sequences for MEDI-524 are incorporated by reference from U.S. Pat. No. 6,818,216, where the sequences for MEDI-524 are as provided in the sequence listing of U.S. Pat. No. 6,818,216 in the following sequence positions: VH CDR1 (SEQ ID NO. 10), VH CDR2 (SEQ ID NO. 19), VH CDR3 (SEQ ID NO:

20), VL CDR1 (SEQ ID NO: 39); VL CDR2 (SEQ ID NO: 5); VL CDR3 (SEQ ID NO: 6).

In some embodiments, the antibody to be isolated is a different commercially available antibody, chosen from of adalimumab (Humira®, Abbott Laboratories), eculizumab (Soliris®, Alexion Pharmaceuticals), rituximab (Ritixan®, Roche/Biogen Idec/Chugai), infliximab (Remicade®, Johnson & Johnson/Schering-Plough/Tanabe), trastuzumab (Herceptin®, Roche/Chugai), bevacizumab (Avastin®, Chugai/Roche), palivizumab (Synagis®, MedImmune/Abbott), alemtuzumab (Campath®, Genzyme), and motavizumab (Numax®, MedImmune).

In some embodiments, antibodies other than Synagis® are manufactured using the present methods. Antibodies can also include chimeric, single chain, and humanized antibodies. Examples of antibodies can include commercialized antibodies, such as natalizmab (humanized anti-a4 integrin monoclonal antibody), humanized Anti-Alpha V Beta 6 monoclonal antibody, humanized anti-VLA1 IgG1 kappa monoclonal antibody; huB3F6 (humanized IgG1/kappa monoclonal antibody). In some embodiments, the antibody is a recombinant monoclonal antibody directed against CD-3, CD-4, CD-8, CD-19, CD-20, CD-34, CD-52, HER-4, HER-3, HER-2, TNF, and/or VLA-4. In some embodiments, the antibody is a recombinant monoclonal antibody directed against an epitope in the A antigenic site of the F protein of RSV.

An antibody produced by the method herein can be from any animal origin including birds and mammals. In some embodiments, the antibody purified by the methods may be human, murine (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins. See, e.g., U.S. Pat. No. 5,939,598 by Kucherlapati et al.

An antibody can include, e.g., native antibodies, intact monoclonal antibodies, polyclonal antibodies, multispecific antibodies (e.g., bispecific antibodies) formed from at least two intact antibodies, antibody fragments (e.g., antibody fragments that bind to and/or recognize one or more antigens), humanized antibodies, human antibodies Jakobovits et al., Proc. Natl. Acad. Sci. USA 90:2551 (1993); Jakobovits et al., Nature 362:255-258 (1993); Bruggermann et al., Year in Immunol. 7:33 (1993); U.S. Pat. Nos. 5,591,669 and 5,545,807), antibodies and antibody fragments isolated from antibody phage libraries (McCafferty et al., Nature 348:552-554 (1990); Clackson et al., Nature 352:624-628 (1991); Marks et al., J. Mol. Biol. 222:581-597 (1991); Marks et al., Bio/Technology 10:779-783 (1992); Waterhouse et al., Nucl. Acids Res. 21:2265-2266 (1993)). An antibody can be recombinantly fused to a heterologous polypeptide at the N- or C-terminus or chemically conjugated (including covalently and non-covalently conjugations) to polypeptides or other compositions. For example, an antibody can be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

In another embodiment, the protein concentration of the recombinant protein in the composition comprising a recombinant protein is from about 0.1 mg/mL to about 1000 mg/mL, from about 10 mg/ml to about 500 mg/ml, from about 50 mg/ml to about 250 mg/ml, from about 75 mg/ml to about 150 mg/ml. In one embodiment, the recombinant protein concentration is about 100 mg/mL. In another embodiment, the recombinant protein concentration is about 10 mg/mL, about 50 mg/ml, about 75 mg/ml, about 100 mg/ml, about 125 mg/ml, about 150 mg/ml, about 250 mg/ml, about 500 mg/ml, about 1000 mg/ml.

IV. Incorporation into a Production Process

The present degassing method may be incorporated into multiple different production processes for compositions comprising recombinant proteins. While certain production processes are outlined here, the present degassing method may be included in other manufacturing processes to achieve the benefits outlined herein. In one embodiment, a bubbles in the fill line are present if the degassing method is not used and/or a ring is present on the vial or other container if a degassing method is not used.

In one embodiment, at least one surfactant is present in the composition. In one embodiment, the production process does not add surfactant to the composition. In one embodiment, there is no surfactant present in the composition.

In one embodiment, a production process is outlined in WO2014071344A2, which is herein incorporated by reference in its entirety for the methods of isolating Synagis® in the absence of benzonase.

In one embodiment, a production process includes a method of isolating Synagis® from a composition comprising Synagis®, the method comprising:

a. performing an ion exchange chromatography process on the composition;

b. performing an affinity purification process on the composition; and c. performing a filtration process on the composition;

d. degassing the composition before filling vials with the composition, wherein a final product comprising Synagis® results from (a), (b), (c), and (d) wherein the final product is suitable for administration to a human and has a DNA concentration of ≤0.5 pg/mg, and wherein the method does not comprise adding benzonase to the composition.

In another embodiment, a production process includes a method of isolating Synagis® from a composition comprising Synagis®, the method comprising:

a. performing a cation exchange chromatography process on the composition to form a first product comprising Synagis®;

b. adding a buffer to the first product to form a buffered product;

c. performing an affinity purification process on the buffered product to form a second product comprising Synagis®;

d. performing a filtration process on the second product to form a third product comprising Synagis®;

e. performing a viral inactivation process on the third product; and f. formulating the third product to form a final product comprising Synagis®, wherein the final product is suitable for administration to a human and has a DNA concentration of ≤0.5 pg/mg; and g. degassing the composition before filling vials with the composition, wherein the method does not comprise adding benzonase to the composition.

In another aspect, a production process includes a method of isolating Synagis® from a composition comprising Synagis®, the method comprising at least three of (a)-(e) and further comprising (f):
- a. performing a cation exchange chromatography process on the composition;
- b. performing an affinity purification process on the composition;
- c. performing an ultrafiltration process on the composition;
- d. performing a viral inactivation process on the composition; and
- e. performing an anion exchange chromatography process on the composition;
- f. degassing the composition before filling vials with the composition, wherein the product resulting from the at least three of (i)-(v) and (vi) comprises Synagis® and is suitable for administration to a human and has a DNA concentration of ≤0.5 pg/mg; and wherein the method does not comprise adding benzonase to the composition.

Methods of isolating the antibody can include various means known in the art, e.g., centrifugation, size exclusion chromatography, ion exchange chromatography, affinity chromatography, filtration, and combinations of the above, just to name a few. The method of purification is generally chosen based on a characteristic of the antibody that distinguishes it from one or more impurities that coexist with the antibody in a composition.

The methods as described herein can utilize an ion exchange chromatography process to isolate the antibody, e.g. Synagis®, from one or more impurities in the composition. Ion exchange chromatography refers to both cation exchange chromatography and anion exchange chromatography. For the purposes herein, "cation exchange chromatography" refers to any method by which a composition comprising the antibody and one or more impurities can be separated based on charge differences using a cation exchange matrix. A cation exchange matrix generally comprises covalently bound, negatively charged groups. Weak or strong cation exchange resins may be employed. Commonly, strong cation exchange resins comprise supported organic groups comprising sulphonic acid or sulphonate groups, depending upon the pH. Weak cation exchange resins commonly comprise supported organic groups comprising carboxylic acid or carboxylate groups, depending upon the pH. In certain embodiments, multimodal cation exchange resins can be used, which incorporate additional binding mechanisms as well as the ionic interactions, for example one or more of hydrogen bonding interactions and hydrophobic interactions. Examples of suitable cation exchange resins are well known in the art, and can include, but are not limited to Fractogel®, carboxymethyl (CM), sulfoethyl (SE), sulfopropyl (SP), phosphate (P) and sulfonate (S), PROPAC WCX10™ (Dionex), Capto™ S, S-Sepharose FF, Fractogel® EMD SO$_3$M, Toyopearl® Megacap® II SP 550C, Poros® 50 HS, and SP-sepharose matrix. In some embodiments, the cation resin is chosen from Capto™ S, S-Sepharose FF, Fractogel® EMD SO$_3$M, Toyopearl® Megacap® II SP 550C, Poros® 50 HS. In certain embodiments, the cation resin is Poros® 50 HS. In some embodiments, more than one cation exchange chromatography process can be employed on the composition. In some embodiments, the cation exchange chromatography process is employed in binding mode with respect to the antibody, i.e., is employed such that the antibody of interest is adsorbed to the cation exchange matrix, while one or more impurities are not adsorbed, thus isolating the antibody from the impurity. In some embodiments, the cation exchange matrix is washed one or more times with a buffer to remove additional impurities before the adsorbed antibody is removed from the cation exchange matrix. After one or more impurities have been removed from a composition employing cation exchange chromatography in binding mode, the adsorbed antibody can be eluted from the cation exchange matrix. Methods of eluting the antibody from the cation exchange are dependent on the matrix and are known to those of skill in the art.

Alternatively, in some embodiments the cation exchange process can be employed in flow-thru mode, i.e., is employed such that the antibody of interest is not adsorbed to the cation exchange matrix, while one or more impurities is adsorbed to the matrix, thus isolating the antibody from the impurity. In flow thru mode, one or more impurities are adsorbed to (or impeded by) the cation exchange matrix, and the antibody passes thru the matrix into the flow thru solution.

In some embodiments, the ion exchange chromatography process is an anion exchange chromatography process. For the purposes herein, "anion exchange chromatography" refers to any method by which a composition comprising the antibody and one or more impurities can be separated based on charge differences using an anion exchange matrix. An anion exchange matrix generally comprises covalently bound, positively charged groups. Strong or weak anion exchange matrices can be employed. Examples of strong anion exchange matrices include, e.g., those having a quarternary ammonium ion. Examples of weak anion exchange matrices include, e.g., those having either a tertiary or secondary amine functional group, such as DEAE (diethylaminoethyl). In certain embodiments, multimodal anion exchange matrices can be used, which incorporate additional binding mechanisms as well as the ionic interactions, for example one or more of hydrogen bonding interactions and hydrophobic interactions. Examples of suitable anion exchange matrices are known in the art, and can include, but are not limited to Super Q, Sartobind® Q, Natrix® Q, Chromasorb™ Q, and Mustang® Q. In some embodiments, the anion exchange matrix is Super Q. In some embodiments, more than one anion exchange process can be employed on the composition.

In some embodiments, the anion exchange chromatography process is employed in binding mode with respect to the antibody, i.e., is employed such that the antibody of interest is adsorbed to the anion exchange matrix, while one or more impurities do not bind, thus isolating the antibody from the impurity. In some embodiments, the anion exchange matrix is washed one or more times with a buffer to remove additional impurities before the adsorbed antibody is removed from the anion exchange matrix. After one or more impurities have been removed from a composition employing anion exchange chromatography in binding mode, the adsorbed antibody can be removed from the anion exchange matrix.

In some embodiments, the anion exchange process is employed in flow-thru mode, i.e., is employed such that the antibody of interest is not significantly adsorbed to the anion exchange matrix, while one or more impurities is adsorbed (or impeded) to the matrix, thus isolating the antibody from the impurity. After one or more impurities have been removed from a composition employing anion exchange chromatography in flow through mode, the adsorbed antibody can be obtained from the flow through of the anion exchange matrix.

In some embodiments, the methods can comprise more than one ion exchange process, e.g., a second ion exchange process. In some embodiments, the first ion exchange process is a cation exchange process and the second ion exchange process is an anion exchange process. In some embodiments, three ion exchange chromatography processes are used.

The methods described herein can utilize an affinity purification process to isolate the antibody from one or more impurities in the composition. As used herein, "affinity purification process" or "affinity chromatography" refers to a separation method whereby an antibody is purified by virtue of its specific binding properties to an affinity ligand for an antibody. In some embodiments, the functional affinity ligand can be immobilized on a solid or semi-solid support, so that when a composition comprising the antibody is passed over the ligand and the solid support, the antibody having a specific binding affinity to the ligand adsorbs to the ligand, and one or more other components of the composition are not adsorbed, or are bound at a lower affinity, and can be separated from the antibody. In some embodiments, the solid support comprising the ligand is washed one or more times with a buffer to remove additional impurities before the adsorbed antibody is removed from the ligand and the support. After one or more impurities have been removed, the adsorbed antibody can be removed from the ligand and the support, resulting in isolation of the antibody from the original composition.

Methods of removing the antibody from the ligand and support are dependent on the ligand and are known to those of skill in the art and can include, e.g., changes in environment, e.g., pH, addition of chaotropic agents or denaturants, or addition of commercially available elution buffers. In some embodiments, more than one affinity purification processes can be employed on the composition comprising the antibody.

Various affinity purification processes are know in the art, and include, but are not limited to, the use of Protein A, Protein G, or combinations thereof as ligands. The ligands can be immobilized on various supports, e.g., a resin. In some embodiments, the affinity purification process comprises a Protein A purification process, e.g., wherein the antibody is adsorbed to Protein A, and the Protein A is coupled to an immobilized support, e.g., a resin. Various Protein A affinity systems are available commercially, and include MabSelect™, MabSelect™ SuRe™, MabSelect Xtra™, Sepaharose CL-4B, ProSep® vA, ProSep® vA Ultra, Ceramic HyperD®, and Poros® MabSelect™. In some embodiments, the affinity purification process comprises a Protein G purification process, e.g., where the antibody is adsorbed to Protein G, and the protein G is couple to an immobilized support, e.g., a resin. Ready-to-use resins and purification kits are known to those in the art.

In some embodiments, the ligand is an antigen, e.g., a peptide or hapten, coupled to an immobilized support, wherein the antibody is selectively adsorbed to the antigen. Activated resins and complete kits for preparing immobilized antigens via a variety of chemistries are known to those in the art.

In some embodiments, other ligands can be used, and are known in the art. See, e.g., the reference texts *Affinity Separations: A Practical Approach* (Practical Approach Series), Paul Matejtschuk (Editor), Irl Pr (1997); and *Affinity Chromatography*, Herbert Schott, Marcel Dekker, New York (1997). For example, affinity ligands can include antibodies and antibody fragments, natural ligands or ligand analogs (e.g., for a particular receptor), and natural binding partners or analogues thereof (e.g., for a multisubunit complex).

In some embodiments, the composition undergoes multiple cycles of the affinity purification process.

The methods can utilize a filtration process to isolate the antibody from one or more impurities in the composition. The terms "filtration process," and "filtering" refer to the process of removing suspended particles from a composition by passing the composition through one or more semi-permeable filter (or membrane or medium) of a specified pore size diameter, wherein larger molecules (generally $>10^3$-$10^6$ Da) are retained on the filter, while water and lower molecular weight molecules pass through the filter.

In some embodiments, after filtration the antibody is substantially in the permeate stream (i.e., it passes through the filter pores and is collected), while an impurity (e.g., cellular debris, DNA, and/or host cell protein) is substantially in the retentate stream. In some embodiments, after filtration the antibody is substantially in the retentate stream, while an impurity is substantially in the permeate stream. The term "permeate stream" when referring to filtration, refers to the fraction of the composition that passes through the filter pores during filtration. The term "retentate stream" when referring to filtration, refers to the fraction of the composition that remains on the filter or that does not pass through the filter pores during filtration.

Suitable types of filtration apparatuses are known to those in the art and can be selected based on various factors, e.g., the molecular weight of the antibody to be filtered, the amount and size of the components of the composition to be filtered, the volume of the composition to be filtered, and the cell density and viability of the composition to be filtered. In some embodiments, filters, such as membrane ultrafilters, plate ultrafilters, cartridge ultrafilters, bag ultrafilters, or vacuum ultrafilters can be used. Commercially available ultrafilters that can be employed are manufactured by various vendors such as Millipore Corporation (Billerica, Mass.), Pall Corporation (East Hills, N.Y.), GE Healthcare Sciences (Piscataway, N.J.), and Sartorius Corporation (Goettingen, Germany).

In another mode, an ultrafiltration process comprises a process of retaining the recombinant protein in the composition and concentrating it by allowing solute to flow through the ultrafiltration device.

In some embodiments, the method further comprises a virus inactivation process. As used herein, "virus inactivation process" refers to the (1) inactivation of a virus, (2) physical removal of a virus, or (3) combinations thereof. When referring to the inactivation of viruses, the viruses may remain in the final product, but in a non-infective form. In some embodiments, the virus inactivation process comprises incubating the composition, e.g., at a low pH sufficient to inactivate (e.g., denature) a virus. In some embodiments, the virus inactivation process comprises adjusting the pH of the composition to a pH of about 5.0 or less, about 4.5 or less, about 4.0 or less, or about 3.5 or less. In some embodiments, the pH of the composition is adjusted to a pH of about 1.0 to about 5.0, about 1.5 to about 4.5, about 2.0 to about 4.0, or about 2.5 to about 3.5. In some embodiments, the virus inactivation process comprises incubating the composition at a pH less than about 4.0, about 2.8 to about 3.2, or about 3.0. In some embodiments, the virus inactivation process comprises incubating the composition comprising the antibody at a pH of less than 4.0.

The pH of the composition can be lowered for various lengths of time sufficient for viral inactivation to occur, e.g., about 1 minute to about 2 hours, or about 10 minutes to about 90 minutes, about 20 minutes to about 80 minutes, about 25 minutes to about 35 minutes, or about 30 minutes. Methods of altering pH are known to those of skill in the art.

In some embodiments, the viral inactivation process can include treatment with solvents or detergents, irradiation, and/or brief exposures to high temperatures sufficient to inactivate a virus. Methods of viral inactivation by these means are known to those of skill in the art, and one of skill in the art can select an appropriate treatment to be used during antibody isolation.

In some embodiments, the viral inactivation process can include the physical removal of the virus from the composition by means of nanofiltration. The term "nanofiltration" refers to the physical passing of the composition through a matrix, e.g., filter, membrane, etc., such that the antibody in the composition is separated from one or more viruses. In some embodiments, nanofiltration comprises passing the composition through a matrix having a pore size of less than 75 nm, 50 nm, 40 nm, 35 nm, 30 nm, 25 nm, 20 nm or 15 nm. Various nanofilters are available commercially and are known in the art.

In some embodiments, two separate virus inactivation processes are utilized, e.g., (1) a virus inactivation process comprising incubating the composition at a pH of less than 4.0, and (2) a virus inactivation process comprising a subjecting the composition to a nanofiltration process. In some embodiments, three or more separate virus removal processes are utilized.

Various buffer systems can be used during the isolation process. In some embodiments, the buffer is chosen from MES buffer, Tris buffer, sodium phosphate buffer, phthalate buffer, citrate buffer, acetate buffer and combinations thereof. In some embodiments, the buffer is a Tris buffer, optionally a Tris/magnesium buffer.

EXAMPLES

Example 1. A 65 L Tank Degassing Experiment

Studies were performed to determine the impact of vacuum, volume, and time on degassing. Using a 65 L tank, drug substance was filtered into a clean tank and pressurized to 20 psig and stored at 2-8° C. for 1 week to increase dissolved oxygen. For degassing, a vacuum was applied to achieve a target vacuum, the valve closed and degassed for a specified duration.

The tank outlet was attached directly to a piston pump inlet. A clear tubing line extended from the pump outlet to a nozzle that would fill a container to simulate the filling of vials. The line was configured in an upside down U shape. The tubing line was purged at the beginning of the fill to ensure no bubbles in the line. The fill was started and the bubble formation in the loop and at the pump outlet was monitored. The time and volume of drug substance dispensed at the first instance of bubble formation was also recorded.

Example 2. Impact of Vacuum on Degassing a 40 L Solution in a 65 L Tank

Following the protocol of Example 1, the impact of vacuum on degassing of a composition comprising 1 mg/ml of MEDI-524 was evaluated. The degassing pressure was varied, with values at 99, 268, and 505 mbar. The time for degassing spanned from 1 to 4 days, as noted in the table below.

TABLE 2

Impact of Vacuum on Degassing

| Vacuum | 99 mBar | 268 mBar | 505 mBar |
| --- | --- | --- | --- |
| Degassing Time (hr) | 46 | 72 | 94 |
| Fill Line bubbles | No | No | Yes |

Bubbles were observed in the composition degassed at 505 mbar. This shows that a combination of vacuum and time may be employed to degas a solution and that even at longer times, a weak vacuum may not be efficient at degassing.

Example 3. Impact of Vacuum on Degassing a 40 L Solution in a 65 L Tank Over a Two-Day Period Following the protocol of Example 1, the impact of vacuum on degassing of a composition comprising 1 mg/ml of MEDI-524 was evaluated. Degassing pressure was varied, with values at 99 and 268 mbar. Degassing was conducted over a 2-day period, though the precise number of hours varied slightly between the samples, as shown below.

TABLE 3

Impact of Vacuum on Degassing Over a Two-Day Period

| Pressure | 99 mbar | 268 mbar |
| --- | --- | --- |
| Degassing Time (hr) | 46 | 48 |
| Fill Line bubbles | No | Yes |

No bubbles were seen in the composition degassed at 99 mbar, yet a significant amount of bubbles were seen in the composition degassed at 268 mbar. FIGS. 1A and B show the fill line, with FIG. 1A showing a picture of the fill line at the start of the fill process for the composition degassed at 268 mbar and FIG. 1B showing a picture of the end of the fill process (8.4 kg fill) for the composition degassed at 268 mbar. Bubbles in the fill line downstream of the piston pump can result in fill weight variation in a commercial manufacturing and vial-filling process, can require fill interruption, and line purge. This can result in a significant loss of product.

Example 4. Impact of Volume on Degassing

Following the protocol of Example 1, the impact of volume on degassing of a composition comprising 1 mg/ml of MEDI-524 was also evaluated. The degassing pressure was varied, with values at 99 and 268 mbar. The time for degassing spanned from 72 hours (for the degassing pressure of 268 mbar) and 46 hours (for the degassing pressure of 99 mbar).

TABLE 4

Impact of Volume on Degassing

| Vacuum (mbar) | 268 | | 99 | |
| --- | --- | --- | --- | --- |
| Volume | 40 L | 60 L | 40 L | 60 L |
| Degassing Time (hr) | 72 | 72 | 46 | 46 |
| Fill Line bubbles | No | Yes | No | Yes |

For the 60 L solution, fill line bubbles were observed from the beginning of the fill for both the 99 and 268 mbar samples. Bubbles also increased with increasing volume dispensed. The data shows that volume can impact the ability to degas a solution.

Figure 2:
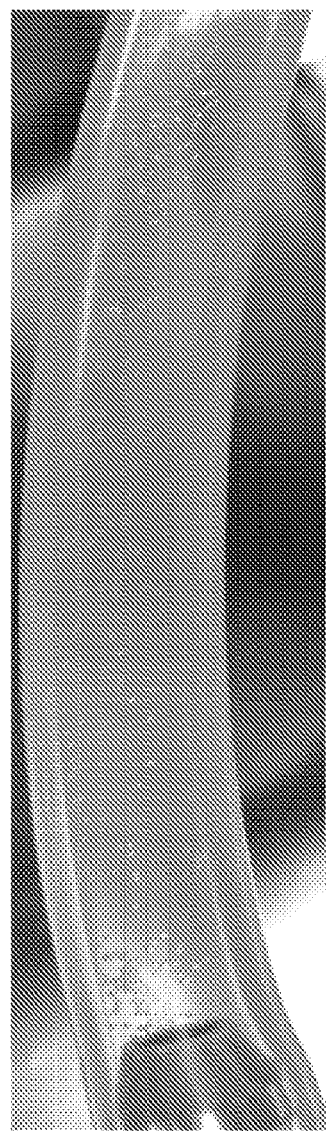
FIGS. 2A-B show, in the same study of the impact of volume on degassing, and for the composition degassed at 268 mbar, the fill line bubbles at ~400 mL fill (panel A) and ~1400 mL fill (panel B). More bubbles are visually apparent later in the fill process for the composition degassed at 268 mbar.
Figure 2:
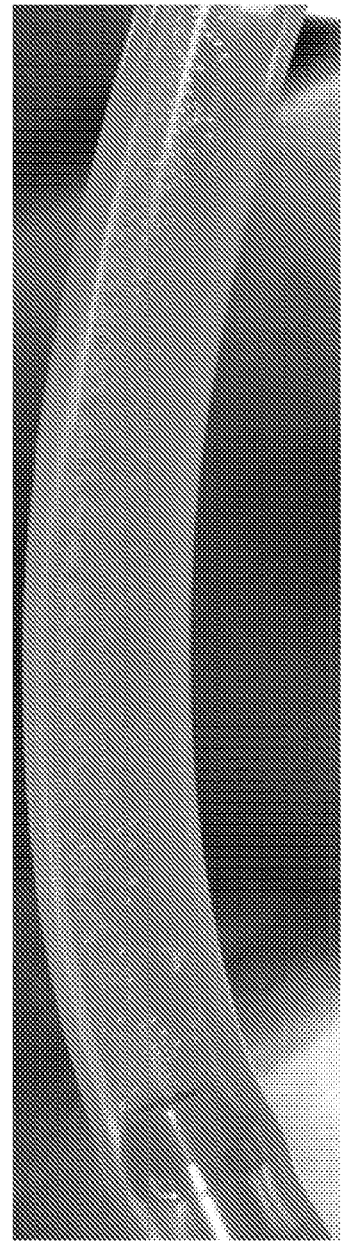

FIGS. 2A and B show the fill line bubbles at ~400 mL fill (FIG. 2A) and ~1400 mL fill (FIG. 2B). More bubbles are visually apparent later in the fill process for the composition degassed at 268 mbar.

Example 5: Impact of Time on Degassing

Following the protocol of Example 1, the impact of time on degassing of a composition comprising 1 mg/ml of MEDI-524 was also evaluated at a fixed volume of 40 L for the solution and a fixed pressure of 99 mbar. The degassing time varied, with conditions at 24 hours and 46 hours (simulating approximately 1 or 2 days).

TABLE 5

Impact of Time on Degassing

| Volume | 40 L | 40 L |
|---|---|---|
| Degassing Time (hr) | 24 | 46 |
| Fill Line bubbles | Yes | No |

Figure 3:
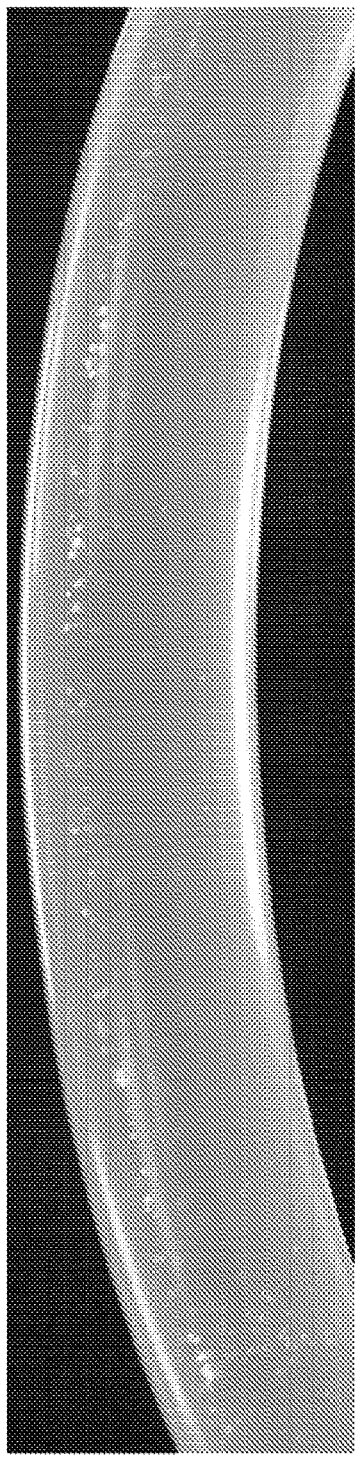
FIGS. 3A-B show, in a study on the impact of time on degassing, a photograph of the fill line for the 1 day degassed composition, with FIG. 3A showing a picture of the fill line at ~300 mL fill and FIG. 3B showing a picture of the fill line at ~650 mL fill. More bubbles can be visualized at the ~650 mL fill point.
Figure 3:
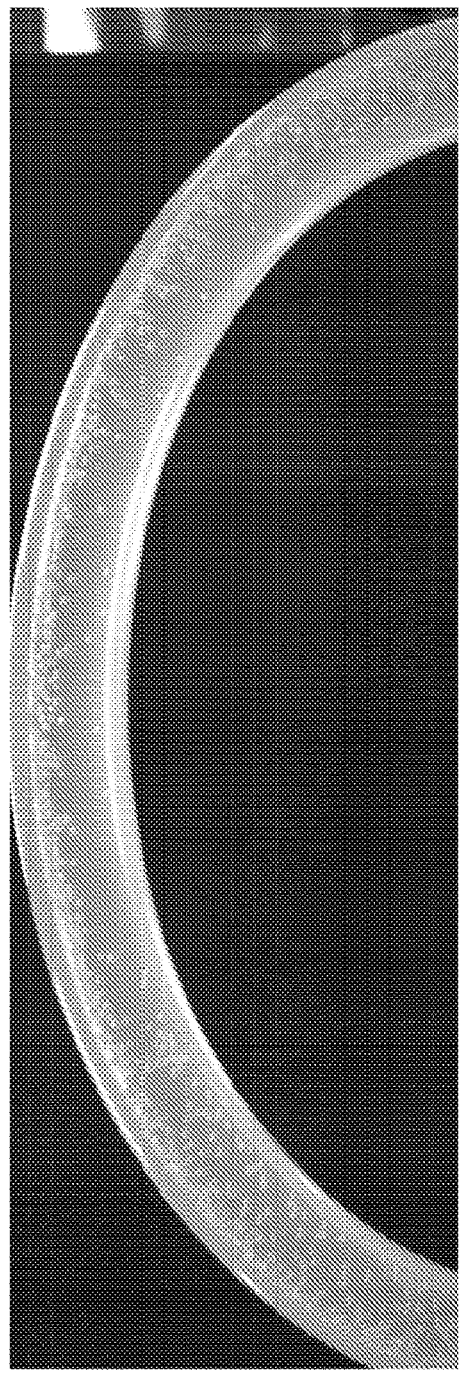

A photograph of the fill line for the 1 day degassed composition is shown in FIGS. 3A and B, with FIG. 3A showing a picture of the fill line at ~300 mL fill and FIG. 3B showing a picture of the fill line at ~650 mL fill. More bubbles can be visualized at the ~650 mL fill point.

Example 6. Impact of Protein Concentration on Degassing

Following the protocol of Example 1, the impact of protein concentration on degassing of a composition was also evaluated, at a fixed solution volume of 40 L, a fixed pressure of 99 mbar, and for a time of 2 days (with the actual number of hours varying slightly as shown below). Both a 1 mg/ml concentration (MEDI-524) and a 100 mg/ml (Synagis®) were evaluated. No bubbles were observed in either of the test conditions. Results are shown in Table 6.

TABLE 6

Impact of Protein Concentration on Degassing

| Protein Concentration | 1 mg/mL | 100 mg/mL |
|---|---|---|
| Degassing Time (hr) | 46 | 47.5 |
| Fill Line bubbles | No | No |

This shows that protein concentration has no or minimal impact on bubble formation in the fill lines.

Example 7. Degassing Predictions from Applying the Bubble Indicator

To predict the incident of bubble formation the following parameters were considered and applied to a bubble indicator formula:

$$BI = (h_a * t * 1000)/(h_l * P * V)$$

Volume of solution (V in mL)
Degassing Vacuum (P in mbar)
Degassing Time (t in hr)
Height of Liquid ($h_l$ in cm)—calculated assuming tank is cylinder
Height of Air/Headspace ($h_a$ in cm)

The bubble indicator was calculated for various experimental conditions and compared to actual empirical observations of whether bubbles were present in fill lines after degassing. Results are shown in Table 7. Except when noted, degassing was performed in a 65 L tank.

TABLE 7

Comparison of Degassing Predictions to Empirical Data

| | Volume (L) | Vacuum (mBar) | Degassing Time (day) | Bubbles (Y/N) | B.I |
|---|---|---|---|---|---|
| 1 mg/mL | 40 | 99 | 1 | Y | 5.5 |
| MEDI-524 | 40 | 99 | 2 | N | 10.6 |
| (Development) | 40 | 268 | 3 | N | 5.9 |
| | 40 | 505 | 4 | Y | 4.1 |
| | 60 | 268 | 3 | Y | 1.1 |
| | 60 | 99 | 2 | Y | 1.9 |
| Synagis ® Run | 38.8 | 99 | 2 | N | 10.6 |
| (Development) | 45.1 | 133 | 3 | N | 7.0 |
| | 68.1* | | | | |
| Synagis ® | 40 | 100 | 3 | N | 15.8 |
| Runs in | 45.2* | 100 | 3 | N | 28.4 |
| manufacturing | 24.6 | 100 | 3 | N | 60 |
| facility | 44.8* | 100 | 3 | N | 29 |
| | 46.2* | 100 | 3 | N | 26.8 |
| | 26.5 | 100 | 3 | N | 49.7 |
| | 44.4* | 100 | 3 | N | 29.8 |
| | 45.3* | 100 | 3 | N | 28.2 |
| | 29.4 | 100 | 3 | N | 37.9 |

*Degassing was performed in a 125 L tank instead of a 65 L tank.

Based upon this data, a bubble indicator of at least about 5.9 will likely result in no bubbles in fill lines.

Example 8. Synagis® Ring Investigation

Figure 4:
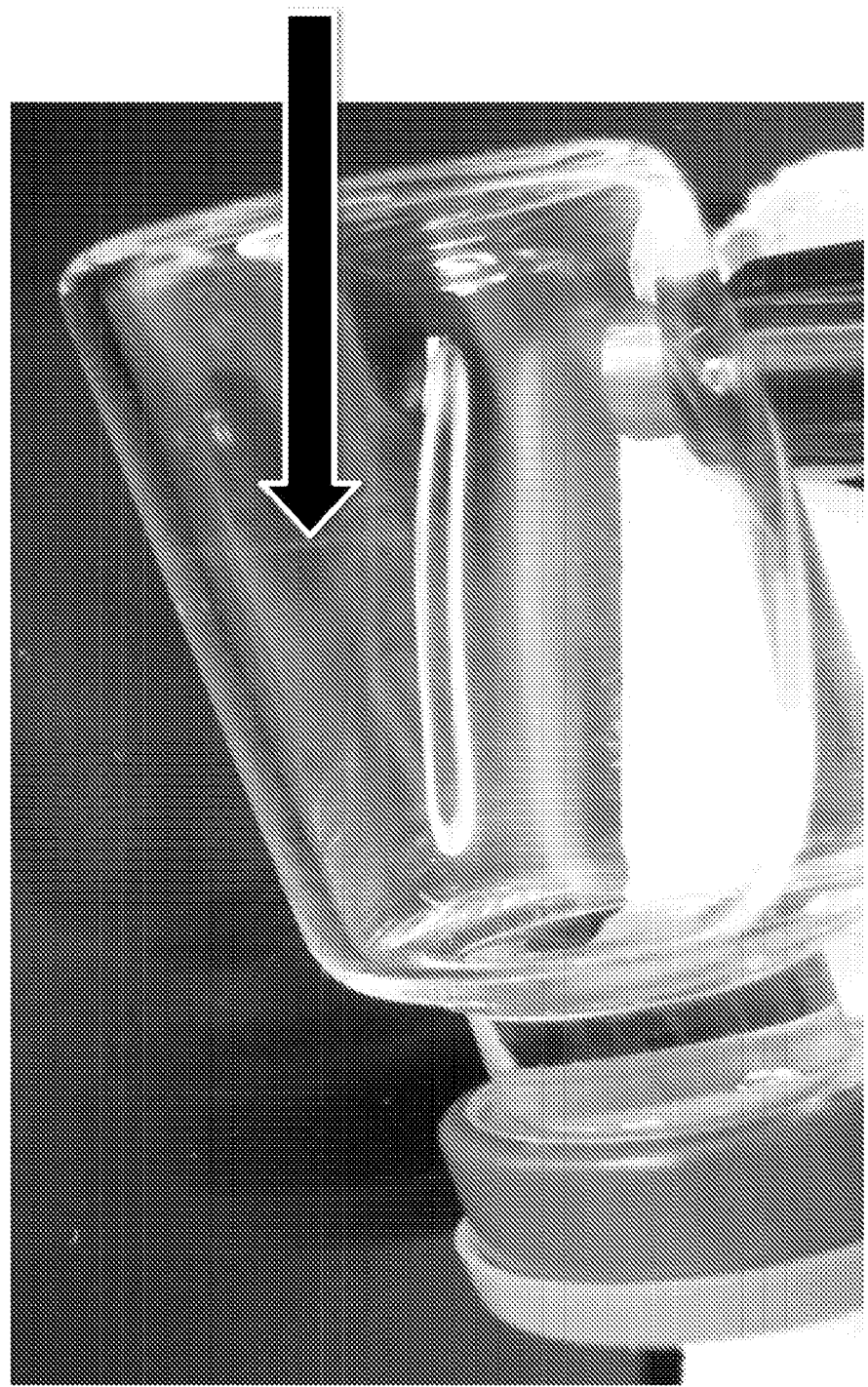
FIG. 4 is a picture of a white ring substantially horizontally shown on the vial glass to the left of the indicator arrow.

Rings have been observed in Synagis® vials, namely for example in the 50 and 100 mg vials). This appears as a very faint white ring located at the air-liquid interface which firmly adheres to the side of the glass wall, as depicted in FIG. 4 as a white ring substantially horizontally shown on the vial glass to the left of the indicator arrow.

In investigations, the following factors have been determined:

dissolved gasses and bubbles are inherent to the drug substance process for Synagis®;
the presence of bubbles and no surfactant leads to ring formation in vials;
drug product fill finish process has no influence on ring formation, with rings formed on drug substance hand-filled directly from tanks;
ring presence has no impact on product quality, but can be a visually-bothersome cosmetic defect;
ring isolation by Tryptic digest shows that the protein in the ring is Synagis®;
ring formation is reproducible at small scale.

It was not, however, expected that bubble formation and the problem of in-line bubbles would be connected to the ring formation because in line bubbles are seen with more molecules than those exhibiting the ring formation.

Figure 5:
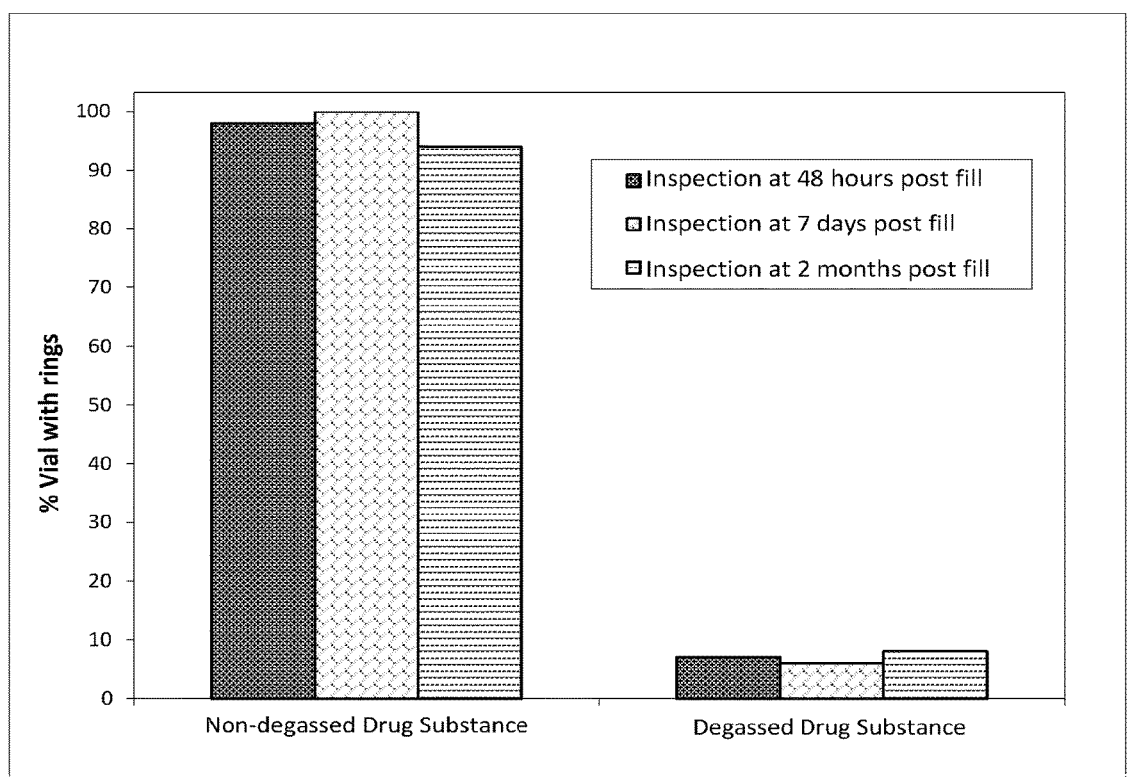
FIG. 5 shows the results of visual inspection of pilot scale batches produced from degassed and non-degassed drug substance.

Surprisingly, degassing has been shown to prevent ring formation. FIG. 5 shows the results of visual inspection of pilot scale batches produced from degassed and non-degassed drug substance. Two 65 L stainless steel tank each containing approximately 20 L palivizumab DS were used for the study. One of tank was stored under positive pressure (non-degassed drug substance) and the second tank was stored under vacuum (degassed drug substance). Both degassed and non-degassed DS were filled into 3 cc clear line glass vials using M&O Perry filter with stainless steel rotary piston pump. Approximately 387 vials were filled from de-gassed DS and 389 vials were filled non-degassed DS. All vials were visually inspected at 48 hours, 7 days, and 2 months post fill against black and white background to detect rings.

Example 9. Synagis® Ring Composition

An evaluation was undertaken to determine the composition of the ring forming on the wall of the Synagis® vials. FTIR was used to identify the ring isolate harvested on a filter surface. The sample, prepared as described above, was analyzed using an FTIR microscope. The harvest showed IR signatures consistent with protein (amide-I band; 1600-1700 $cm^{-1}$ and amide-II band; 1510-1580 $cm^{-1}$) and polydimethyl siloxane (1260 $cm^{-1}$). A second derivative of the amide II band showed a dominant band at 1638 $cm^{-1}$ corresponding to native beta sheet structures typically observed in native IgG molecules. These results indicate that the ring protein is composed of native beta sheet structures. Heat or shear stress IgG1 would shift the main peak of the second derivative to 1628 $cm^{-1}$, which indicates intermolecular interactions exhibited with aggregation (either soluble or insoluble). FTIR shows that the ring contains protein and silicone oil.

Figure 6:
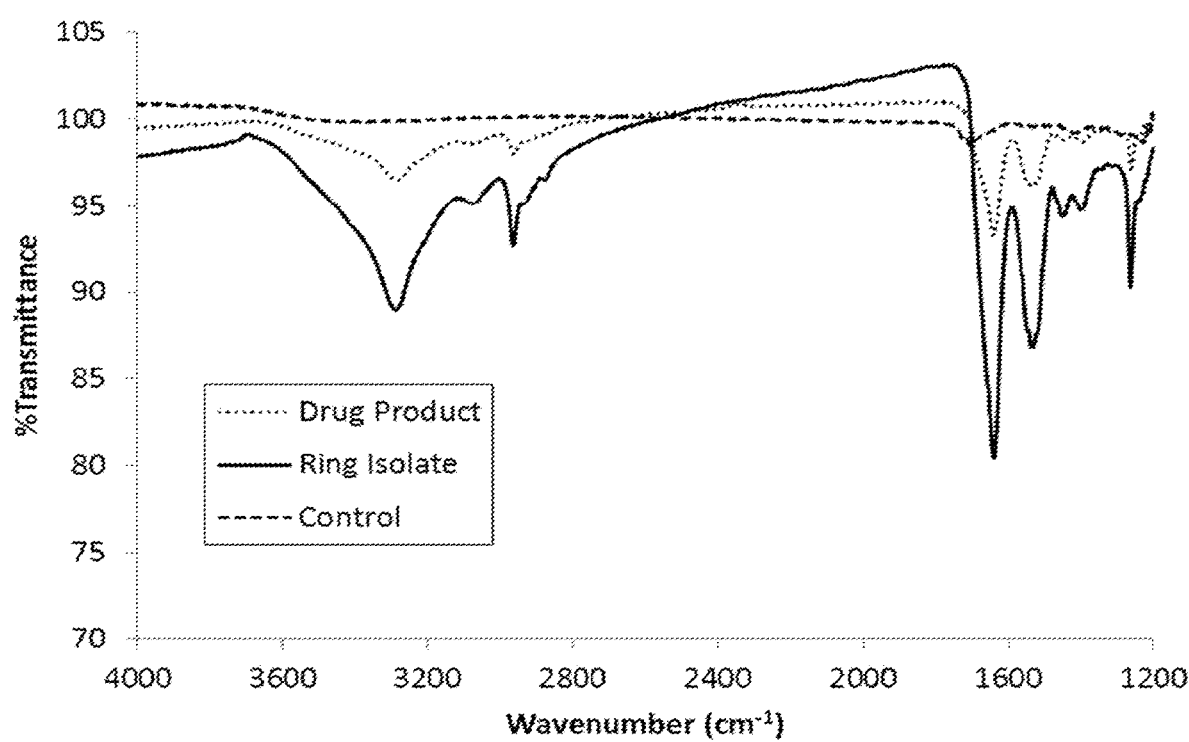
FIG. 6 shows the results of the evaluation of the secondary structure of protein isolated from the ring assessed by second derivative analysis of the amide-I peak. The protein in the ring isolate has a native conformation as determined by FTIR.

The secondary structure of protein isolated from the ring was assessed by second derivative analysis of the amide-I peak. The protein in the ring isolate has a native conformation as determined by FTIR. Results are shown in FIG. 6.

Figure 7:
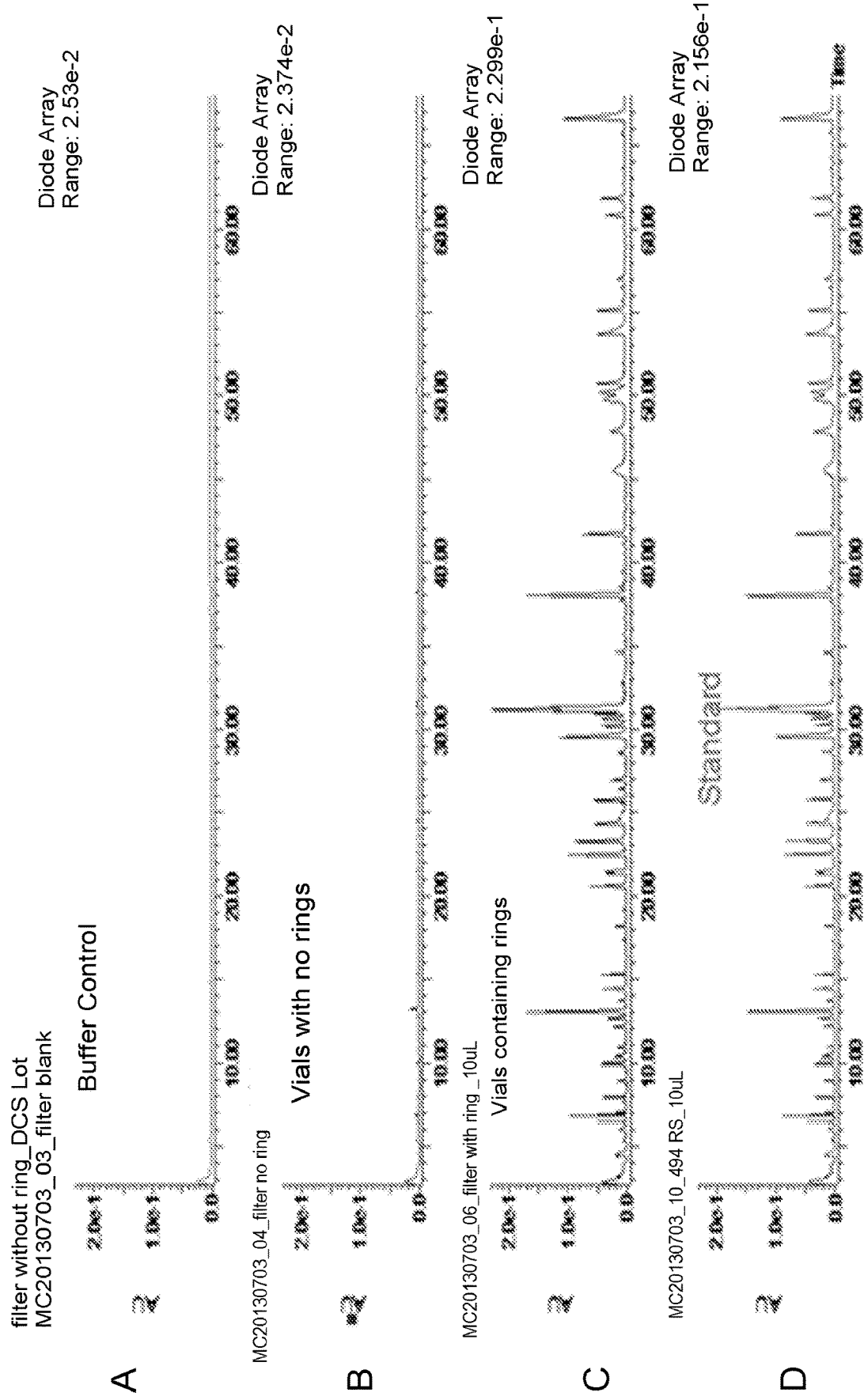
FIGS. 7A-D shows results from tryptic digests that were performed on the protein in the ring of vials containing Synagis®. The tryptic digests show that the protein in the ring is Synagis®.

Tryptic digests were performed on the protein in the ring. The vials were carefully washed with formulation buffer and a separate aliquot was used to isolate the ring by vortexing and forceful pipetting. The harvest was then filtered through a 0.2 µm filter, washed and dried. The filters were incubated in a guanidine solution at 37° C., and the solution reduced and alkylated prior to trypsin digestion. The tryptic digest was separated using a C18 column monitoring UV (Abs 220 nm) and mass (by mass spectrometry, MS). The tryptic peptides were identified relative to a reference standard by mass (corresponding to the amino acid composition) and by fragmentation pattern (using MS/MS). Buffer alone was applied to the filter as a control. The results are shown in FIG. 7. The tryptic digests show that the protein in the ring is Synagis®.

Example 10. Surfactant can Prevent Ring Formation

Drug substance with and without the surfactant PS-80 (0.02%) was pressurized to increase dissolved gasses and bubbles. Vials were filled using a M&O Perry filter with stainless steel rotary piston pump. Approximately 160 mL of palivizumab DS was filtered into each of two 250 mL PETG containers. One of the containers was spiked with 0.02% polysorbate 80 (PS-80). Both PETG containers placed in a custom made stainless steel tank and pressurized with air to 20 psig. Tanks were stored at 2-8° C. on orbital shaker for approximately 43 hours to increase dissolved gasses/bubbles. Approximately 112 vials were filled from each PETG container into 3 cc vials using M&O Perry fill with B&S rotary piston pump. The vials were divided into two sets of 56 vials each and visually inspected at 2 days and 7 days post fill against black and white background to detect rings. Control vials all had rings and none of the PS-80 spiked vials had rings. Bubbles were observed in the fill line with both control and PS-80 spiked drugs substance. This supports the hypothesis that PS-80 prevents protein absorption to the air-liquid interface (bubbles).

Example 11. Embodiments

The following items represent a plurality of potential embodiments.

Item 1. A method of producing vials containing a composition comprising a recombinant protein, the method comprising:
 a. providing a container containing a composition comprising a recombinant protein optionally wherein the container has been stored under positive pressure;
 b. applying a vacuum to the container;
 c. allowing the vacuum to degas the composition; and
 d. filling vials with the degassed composition comprising a recombinant protein.

Item 2. The method of item 1, wherein the recombinant protein is Synagis®.

Item 3. A method of isolating Synagis® from a composition comprising Synagis®, the method comprising:
 a. performing an ion exchange chromatography process on the composition;
 b. performing an affinity purification process on the composition; and
 c. performing an ultrafiltration process on the composition;
 d. degassing the composition before filling vials with the composition,
wherein a final product comprising Synagis® results from (a), (b), and (c), wherein the final product is suitable for administration to a human and has a DNA concentration of ≤0.5 pg/mg, and wherein the method does not comprise adding benzonase to the composition.

Item 4. A method of isolating Synagis® from a composition comprising Synagis®, the method comprising:
 a. performing a cation exchange chromatography process on the composition to form a first product comprising Synagis®;
 b. adding a buffer to the first product to form a buffered product;
 c. performing an affinity purification process on the buffered product to form a second product comprising Synagis®;
 d. performing a filtration process on the second product to form a third product comprising Synagis®;
 e. performing a viral inactivation process on the third product; and
 formulating the third product to form a final product comprising Synagis®, wherein the final product is suitable for administration to a human and has a DNA concentration of ≤0.5 pg/mg;
 f. degassing the composition before filling vials with the composition, wherein the method does not comprise adding benzonase to the composition.

Item 5. A method of isolating Synagis® from a composition comprising Synagis®, the method comprising at least three of (a)-(e) and wherein the method further comprises (f):
 a. performing a cation exchange chromatography process on the composition;
 b. performing an affinity purification process on the composition;
 c. performing an ultrafiltration process on the composition;

d. performing a viral inactivation process on the composition; and
e. performing an anion exchange chromatography process on the composition;
f. degassing the composition before filling vials with the composition, wherein the product resulting from the at least three of (i)-(v) comprises Synagis® and is suitable for administration to a human and has a DNA concentration of ≤0.5 pg/mg; and wherein the method does not comprise adding benzonase to the composition.

Item 6. The method of any one of items 3-5, wherein the step of degassing the composition before filling vials with the composition comprises
  a. providing a container containing a composition comprising a recombinant protein optionally wherein the container has been stored under positive pressure;
  b. applying a vacuum to the container containing a composition comprising a recombinant protein;
  c. allowing the vacuum to degas the composition; and
  d. filling vials with the degassed composition comprising a recombinant protein.

Item 7. The method of any one of items 1-6, wherein the composition comprises:
  a. a heavy chain having the amino acid sequence SEQ ID NO: 1 and a light chain having the amino acid sequence of SEQ ID NO: 6;
  b. a heavy chain variable region of SEQ ID NO:1 or SEQ ID NO: 2 and a light chain variable region of the light chain SEQ ID NO:6; or
  c. a H1 complementarity determining region (CDR) having the amino acid sequence TSGMSVG (SEQ ID NO: 3), a H2 CDR having the amino acid sequence DIWWDDKKDYNPSLKS (SEQ ID NO: 4), a H3 CDR having the amino acid sequence SMITNWYFDV (SEQ ID NO: 5); a L1 CDR having the amino acid sequence KCQLSVGYMH (SEQ ID NO: 7), a L2 CDR having the amino acid sequence DTSKTAS (SEQ ID NO: 8), and a L3 CDR having the amino acid sequence FQGSGYPFT (SEQ ID NO:9).

Item 8. The method of any one of items 1-7, wherein the container containing a composition comprising a recombinant protein has been stored under positive pressure.

Item 9. The method of any one of items 1-8, wherein a vacuum is applied for from about 12 hours to about 5 days.

Item 10. The method of item 9, wherein a vacuum is applied for from about 1 day to about 4 days.

Item 11. The method of any one of items 1-10, wherein a vacuum is applied at from about 50 to about 268 mbar.

Item 12. The method of item 11, wherein the vacuum applied is greater than 50 and less than or equal to 268 mbar.

Item 13. The method of item 11, wherein the vacuum is applied at from about 60 to about 268 mbar.

Item 14. The method claim 11, wherein a vacuum is applied at about 99 or about 268 mbar.

Item 15. The method of any one of items 1-14, wherein a vacuum is applied to a volume of a composition comprising a recombinant protein of from about 20 L to about 250 L or from about 40 L to about 70 L.

Item 16. The method of item 15, wherein a vacuum is applied to a volume of a composition of about 40 L, about 65 L, or about 125 L.

Item 17. The method of item 15, wherein no more than about 50 L of composition is present in an about 65 L tank.

Item 18. The method of item 15, wherein no more than about 76 L of composition is present in an about 125 L tank.

Item 19. The method of item 15, wherein about 45.1 L of composition is present in an about 65 L tank.

Item 20. The method of item 15, wherein about 68.1 L of composition is present in an about 125 L tank.

Item 21. The method of any one of items 1-20, wherein a bubble indicator is at least about 5.9 and is calculated using the following formula:

$$BI=(h_a*t*1000)/(h_1*PV), \text{ wherein}$$

V=volume of solution (mL)
P=degassing vacuum (mbar)
t=degassing time (hr)
$h_1$=height of liquid (cm) (calculated assuming tank is cylinder) and
$h_a$=height of air/headspace (cm).

Item 22. The method of any one of items 1-21, wherein the composition comprising the recombinant protein does not comprise a surfactant.

Item 23. The method of any one of items 1-22, wherein a surfactant is not added to the composition comprising the recombinant protein.

Item 24. The method of any one of items 1-23, wherein the composition, when filled in at least one vial, does not form a ring on the air-liquid-glass interface of the vial.

Item 25. The method of item 24, wherein the composition, when filled in at least one vial, does not form a ring on the surface of the vial.

Item 26. The method of any one of items 1-25, wherein the composition does not comprise bubbles after degassing.

Item 27. The method of item 26, wherein the composition, after degassing and when being filled into at least one vial, does not comprise bubbles in vial fill lines or other tubing used in manufacturing.

Item 28. The method of any one of items 1-27, wherein the protein concentration of the recombinant protein in the composition comprising a recombinant protein is from about 0.1 mg/mL to about 1000 mg/mL.

Item 29. The method of item 28, wherein the protein concentration is about 100 mg/mL.

Item 30. The method of any one of items 1-29, wherein omitting the degassing step results in an accumulation of bubbles in the composition.

Item 31. The method of item 30, wherein omitting the degassing step results in an accumulation of bubbles in the composition in fill lines.

Item 32. The method of any one of items 1-31, wherein omitting the degassing step results in a deposition of particles at air-liquid-glass interface of a vial containing the composition.

Item 33. The method of item 32, wherein the deposition of particles is a deposition comprising the recombinant protein.

Item 34. The method of any one of items 32-33, wherein the deposition of particles forms a ring on the vial.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). In some instances, the term about may include numerical values that are rounded to the nearest significant figure.

What is claimed is:

1. A method of producing vials containing a composition comprising a recombinant protein, the method comprising:
   a. providing a container containing a composition comprising a recombinant protein optionally wherein the container has been stored under positive pressure;
   b. applying a vacuum to the container;
   c. allowing the vacuum to degas the composition; and
   d. filling vials with the degassed composition comprising a recombinant protein,
   wherein a bubble indicator is at least about 5.9 and is calculated using the following formula:

$$BI = (h_a * t * 1000)/(h_l * PV),$$ wherein

V = volume of solution (mL)
P = degassing vacuum (mbar)
t = degassing time (hr)
$h_l$ = height of liquid (cm) (calculated assuming tank is cylinder) and
$h_a$ = height of air/headspace (cm).

2. The method of claim 1, wherein the recombinant protein is palivizumab.

3. The method of claim 1, wherein the composition comprises:
   a. a heavy chain having the amino acid sequence SEQ ID NO: 1 and a light chain having the amino acid sequence of SEQ ID NO: 6;

b. a heavy chain variable region of SEQ ID NO:1 or SEQ ID NO: 2 and a light chain variable region of the light chain SEQ ID NO:6; or c. a H1 complementarity determining region (CDR) having the amino acid sequence TSGMSVG (SEQ ID NO: 3), a H2 CDR having the amino acid sequence DIWWDDKKDYNPSLKS (SEQ ID NO: 4), a H3 CDR having the amino acid sequence SMITNWYFDV (SEQ ID NO: 5); a L1 CDR having the amino acid sequence KCQLSVGYMH (SEQ ID NO: 7), a L2 CDR having the amino acid sequence DTSKLAS (SEQ ID NO: 8), and a L3 CDR having the amino acid sequence FQGSGYPFT (SEQ ID NO:9).

4. The method of claim 1, wherein the container containing a composition comprising a recombinant protein has been stored under positive pressure.

5. The method of claim 1, wherein a vacuum is applied for from about 12 hours to about 5 days.

6. The method of claim 1, wherein a vacuum is applied for from about 1 day to about 4 days.

7. The method of claim 1, wherein a vacuum is applied at from about 50 to about 268 mbar.

8. The method of claim 1, wherein the vacuum applied is greater than 50 and less than or equal to 268 mbar.

9. The method of claim 1, wherein the vacuum is applied at from about 60 to about 268 mbar.

10. The method of claim 1, wherein a vacuum is applied to a volume of the composition comprising a recombinant protein of from about 20 L to about 250 L or from about 40 L to about 70 L.

11. The method of claim 1, wherein a vacuum is applied to a volume of the composition of about 40 L, about 65 L, or about 125 L.

12. The method of claim 1, wherein no more than about 50 L of composition is present in an about 65 L tank.

13. The method of claim 1, wherein no more than about 76 L of composition is present in an about 125 L tank.

14. The method of claim 1, wherein about 45.1 L of composition is present in an about 65 L tank.

15. The method of claim 1, wherein about 68.1 L of composition is present in an about 125 L tank.

16. The method of claim 1, wherein the composition comprising the recombinant protein does not comprise a surfactant.

17. The method of claim 1, wherein a surfactant is not added to the composition comprising the recombinant protein.

18. The method of claim 1, wherein the concentration of the recombinant protein in the composition comprising a recombinant protein is from about 0.1 mg/mL to about 1000 mg/mL.

19. The method of claim 1, wherein the concentration of the recombinant protein in the composition comprising a recombinant protein is about 100 mg/mL.

* * * * *

```
                         SEQUENCE LISTING

<160> NUMBER OF SEQ ID NOS: 9

<210> SEQ ID NO 1
<211> LENGTH: 450
<212> TYPE: PRT
<213> ORGANISM: Artificial sequence
<220> FEATURE:
<223> OTHER INFORMATION: Heavy chain of SYNAGIS humanized antibody

<400> SEQUENCE: 1

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 227
<212> TYPE: PRT
<213> ORGANISM: Artificial sequence
<220> FEATURE:
<223> OTHER INFORMATION: N-terminal antigen binding fragment (Fab) of
      SYNAGIS heavy chain humanized antibody

<400> SEQUENCE: 2

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Cys Thr Cys Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
        210                 215                 220
```

```
Lys Thr His
225

<210> SEQ ID NO 3
<211> LENGTH: 7
<212> TYPE: PRT
<213> ORGANISM: Artificial sequence
<220> FEATURE:
<223> OTHER INFORMATION: Complementary determining region (CDR) H1 of
      SYNAGIS heavy chain humanized antibody

<400> SEQUENCE: 3

Thr Ser Gly Met Ser Val Gly
1               5

<210> SEQ ID NO 4
<211> LENGTH: 16
<212> TYPE: PRT
<213> ORGANISM: Artificial sequence
<220> FEATURE:
<223> OTHER INFORMATION: Complementary determining region (CDR) H2 of
      SYNAGIS heavy chain humanized antibody

<400> SEQUENCE: 4

Asp Ile Trp Trp Asp Asp Lys Lys Asp Tyr Asn Pro Ser Leu Lys Ser
1               5                   10                  15

<210> SEQ ID NO 5
<211> LENGTH: 10
<212> TYPE: PRT
<213> ORGANISM: Artificial sequence
<220> FEATURE:
<223> OTHER INFORMATION: Complementary determining region (CDR) H3 of
      SYNAGIS heavy chain humanized antibody

<400> SEQUENCE: 5

Ser Met Ile Thr Asn Trp Tyr Phe Asp Val
1               5                   10

<210> SEQ ID NO 6
<211> LENGTH: 213
<212> TYPE: PRT
<213> ORGANISM: Artificial sequence
<220> FEATURE:
<223> OTHER INFORMATION: Light chain of SYNAGIS humanized antibody

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125
```

```
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 10
<212> TYPE: PRT
<213> ORGANISM: Artificial sequence
<220> FEATURE:
<223> OTHER INFORMATION: Complementary determining region (CDR) L1 of
      SYNAGIS light chain humanized antibody

<400> SEQUENCE: 7

Lys Cys Gln Leu Ser Val Gly Tyr Met His
1               5                   10

<210> SEQ ID NO 8
<211> LENGTH: 7
<212> TYPE: PRT
<213> ORGANISM: Artificial sequence
<220> FEATURE:
<223> OTHER INFORMATION: Complementary determining region (CDR) L2 of
      SYNAGIS light chain humanized antibody

<400> SEQUENCE: 8

Asp Thr Ser Lys Leu Ala Ser
1               5

<210> SEQ ID NO 9
<211> LENGTH: 9
<212> TYPE: PRT
<213> ORGANISM: Artificial sequence
<220> FEATURE:
<223> OTHER INFORMATION: Complementary determining region (CDR) L3 of
      SYNAGIS light chain humanized antibody

<400> SEQUENCE: 9

Phe Gln Gly Ser Gly Tyr Pro Phe Thr
1               5
```